(12) United States Patent
Allen

(10) Patent No.: US 8,986,747 B2
(45) Date of Patent: Mar. 24, 2015

(54) THRUSH TREATMENT PASTE

(71) Applicant: Todd G. Allen, Vandergrift, PA (US)

(72) Inventor: Todd G. Allen, Vandergrift, PA (US)

( * ) Notice: Subject to any disclaimer, the term of this patent is extended or adjusted under 35 U.S.C. 154(b) by 0 days.

(21) Appl. No.: 14/132,581

(22) Filed: Dec. 18, 2013

(65) Prior Publication Data

US 2014/0178497 A1    Jun. 26, 2014

Related U.S. Application Data

(60) Provisional application No. 61/740,782, filed on Dec. 21, 2012.

(51) Int. Cl.
  *A01N 59/20* (2006.01)
  *A61K 33/34* (2006.01)
  *A61K 47/06* (2006.01)
  *A61K 31/155* (2006.01)
  *A61K 31/191* (2006.01)

(52) U.S. Cl.
  CPC ............... *A61K 47/06* (2013.01); *A61K 31/155* (2013.01); *A61K 31/191* (2013.01); *A61K 33/34* (2013.01)
  USPC ......................................................... 424/637

(58) Field of Classification Search
  None
  See application file for complete search history.

(56) References Cited

U.S. PATENT DOCUMENTS

| | | |
|---|---|---|
| 5,780,064 A | 7/1998 | Meisters et al. |
| 6,716,441 B1 | 4/2004 | Osborne et al. |
| 2001/0021752 A1 | 9/2001 | Watanabe et al. |
| 2005/0271595 A1 | 12/2005 | Brown |
| 2007/0299410 A1 | 12/2007 | Eknoian et al. |
| 2010/0234460 A1 | 9/2010 | Foret et al. |

FOREIGN PATENT DOCUMENTS

EP    2061447    5/2009

OTHER PUBLICATIONS www.wyeth.com/divisions/fort_dodge.asp, 2003.
www.kineticvet.com/products/vetasan.php, 2013.

*Primary Examiner* — Trevor Love
(74) *Attorney, Agent, or Firm* — James Ray & Assoc

(57) ABSTRACT

A composition for treating hoof thrush and similar ailments in horses is composed of a blend of copper sulfate and chlorhexidine dispersed in a viscous carrier. Preferably, the copper sulfate makes up 20 to 45 percent by weight of the final product and the chlorhexidine compound accounts for 1 to 5 percent by weight. A viscous carrier constitutes the balance of the formulation.

7 Claims, No Drawings

THRUSH TREATMENT PASTE

CROSS REFERENCE TO RELATED APPLICATION

This patent application is related to and claims priority from U.S. Provisional Patent Application Ser. No. 61/740,782 filed Dec. 21, 2012.

FIELD OF THE INVENTION

The present invention relates, in general, to antimicrobial creams and ointments and, more particularly, this invention relates to an antimicrobial gel and compositions especially useful for treatment of animals with horny hoof tissue.

STATEMENT REGARDING FEDERALLY SPONSORED RESEARCH AND DEVELOPMENT

N/A

REFERENCE TO SEQUENCE LISTING, A TABLE, OR A COMPUTER PROGRAM LISTING COMPACT DISC APPENDIX

N/A

BACKGROUND OF THE INVENTION

Prior to the conception and development of the present invention, hoof thrush in horses and other hoofed animals has been treated mostly with liquid treatments. Thrush is a very common bacterial or fungal infection that occurs on the hoof of a horse or similar animal. Chlorhexidine ointments in a hydrophilic base are well know for topically treating surface wounds in animals. Commercially available ointments going by the names of Nolvosan® and Vetasan™ ointment are examples of antimicrobials for use with animals and containing chlorhexidine. However, for thrush on horse hooves, these lack the efficacy of the present invention. Also, many of the current treatments are messy to use and cause staining.

In addition, the applicant is unaware of copper sulfate, especially in the relatively high concentrations of the present invention, being a major component in any disclosed treatments of this nature. Ointments or pastes with chlorhexidine in a hydrophobic base such as petrolatum are not known to be available. In U.S. Pat. No. 5,780,064, Meisters et al. discuss various hoof diseases and treatments thereof. Use of copper salts is discussed, but with an upper limit of 20 percent by weight for copper sulfate (Col. 3, line 33). Meisters' disclosed invention is for an aqueous composition comprising copper salt, a quaternary ammonium compound, and a peroxide; and, it is intended primarily for footbaths.

US Patent Published Application 2005/0271595 discloses a long list of antimicrobial agents, of which chlorhexidine is one, and also includes a very long list of emollients, including petrolatum, which can be incorporated into an alcohol/water gel, which is the main ingredient of the prior art disclosure. However, none of the specific examples include even these two components together.

US Patent Application Publication 2010/0234460 discloses treatments of hoof diseases that offer greater resistance to contact with manure. One embodiment incorporates chlorhexidine salts, but in combination with carboxylic acids and surfactants.

U.S. Pat. No. 6,716,441 discloses skin care compositions combining a skin care active with a hydrophobic barrier protectant. It has been known to use copper sulfate as an antifungal in some treatment compositions, but not in combination with the other two components of the present invention. Before now, it has not been known to include copper sulfate in the concentration range of the present invention for any medical treatment.

SUMMARY OF THE INVENTION

The present invention provides a composition for a gel to treat thrush in hoofed animals consisting of copper sulfate and chlorhexidine suspended in a viscous carrier. The presently preferred concentration ranges of active ingredients in the present composition include 1 to 5 percent by weight chlorhexidine salt and 20 to 65 percent by weight copper sulfate, the balance being a viscous carrier. Preferably, the viscous carrier is an aqueous xanthan gum gel, but petrolatum is an acceptable alternative that may be preferred in certain situations.

In one embodiment, the composition comprises a chlorhexidine salt in a range of 0.1 to 5.0 percent by weight, a copper sulfate in a range of 20 to 65 percent by weight of the composition, a carrier comprising a balance of the composition and wherein the composition is configured to treat animal horny tissue.

In another embodiment, the composition comprises a chlorhexidine salt in a range of 1.5 to 2.0 percent by weight, a copper sulfate in a range of 30 to 50 percent by weight of the composition, a petrolatum constituting a balance of the composition, and wherein the composition is configured to treat animal horny tissue.

In a further embodiment, the composition comprises a chlorhexidine salt in a range of 1.5 to 2.0 percent by weight, a copper sulfate in a range of 45 to 65 percent by weight of the composition, a carrier comprising a balance of the composition; the carrier being a blend of about 2.5 percent by weight xanthan gum, about 5 percent by weight isopropanol, and about 92.5 percent by weight water, and wherein the composition is configured to treat animal horny tissue.

OBJECTS OF THE INVENTION

It is, therefore, one of the primary objects of the present invention to provide an effective and practical alternative to liquid treatments for hoof thrush in horses.

Another object of the present invention is to provide an easy-to-apply gel or paste with active ingredients for more effectively treating and/or preventing infections of the horny tissues in animal hooves than previously known.

Still another object of the present invention is to provide a water-resistant paste or gel for topical application of antifungal and antibacterial agents.

Yet another object of the present invention is to jointly provide hoof thrush treatments in a paste, gel, or ointment form with minimal mess.

A further object of the present invention is to provide a composition containing copper sulfate in a range of 20 to 65 percent by weight.

Another object of the present invention is to provide a composition containing chlorhexidine salt in a range of 1 to 5 percent by weight.

Yet another object of the present invention is to provide a composition containing water as a carrier.

In addition to the various objects and advantages of the present invention described with some degree of specificity above, it should be obvious that additional objects and advantages of the present invention will become more readily apparent to those persons who are skilled in the relevant art from the following more detailed description of the invention, particularly, when such description is taken in conjunction with the attached drawing figures and with the appended claims.

DETAILED DESCRIPTION OF A PRESENTLY PREFERRED AND VARIOUS ALTERNATIVE EMBODIMENTS OF THE INVENTION

The present invention is for a composition of active ingredients chlorhexidine and copper sulfate, in effective quantities for treating hoof thrush in horses or similar animals, suspended either in water based carrier, a viscous carrier such as an aqueous xanthan gum solution or, alternatively, a petroleum jelly, also known as white petrolatum. The chlorhexidine may be present as an acetate (diacetate) or as a gluconate (digluconate). Other monocarboxylic acids in the C1 to C6 range, including, for example, formic and hexanoic acid are also acceptable for forming salts with chlorhexidine.

Referring initially to Table 1, the presented ranges for the composition have been found to be effective in treating hoof thrush in horses or similar animals when suspended into a viscous carrier.

TABLE 1

| Component | Percent by Weight |
| --- | --- |
| Chlorhexidine salt | 0.1 to 5.0 |
| Copper sulfate | 20.0 to 65.0 |
| Viscous carrier | Balance |

It is presently preferred that the chlorhexidine salt be in the range of 1.0 to 3.0 percent by weight and the copper sulfate be 40 to 60 percent by weight.

The method of producing the desired product is not very critical. The two active ingredients are measured into the proportionate amount of viscous carrier, and then the mixture is stirred manually or mechanically until the active ingredients appear to be reasonably well dispersed. When petrolatum is the viscous carrier, the mixing operation takes about 3 times as long as with the aqueous xanthan gum when done at a typical room temperature. The chlorhexidine salt can be either as the acetate or gluconate molecule, or a mixture of the two.

The first preference for selling the composition in a viscous form is a squeezable tube, much like of the type provided for toothpaste. The hoof should be moderately clean, and for the petrolatum base, the hoof should also be generally dry. The gel like composition is squeezed out of the tube onto the hoof and spread around by any means available. Initially, once a week treatment may be sufficient, but progress needs to be monitored to see if a more frequent application is warranted.

One example of a presently preferred viscous carrier is a blend of xanthan gum and alcohol in water. The alcohol is added primarily to enhance cold weather performance as the formulation may frequently be employed outside in the winter. A particularly preferred blend would be 2.5 percent by weight xanthan gum, 5 percent by weight isopropanol, and 92.5 percent by weight water. This gel formulation is easy to apply and clean off if desired, but it stays on the affected area longer after being applied than would be the case with a liquid. In some instances, where resistance to water is a more important consideration, such as animals being outdoors in wet or muddy conditions, petrolatum will be the viscous carrier, by itself or in a homogenous ointment blend with up to 50 weight percent of a compatible substances. Straight petrolatum tends to be sensitive to the upper and lower ends of the acceptable temperature range (0 to 100 F), with high stiffness at the low end and, these additional compatible substances can be any fluid that produces a homogeneous blend with the petrolatum when thoroughly mixed together. Some examples of compatible substances would be glycerin, polyethylene glycol, and polypropylene glycol. Thus, a major advantage of the present invention is longer contact time on the affected area with a more effective composition than previously available.

The applicant defines "viscous carrier" as any inert substance or solution having a viscosity greater than that of 1.5 percent by weight xanthan gum in water. It will be understood that numerical values depend on the shear-sensitive nature of xanthan gum solution viscosities. Minor amounts, less than one percent, of additives may be included in any of the formulations for various reasons, for example, chlorine dioxide and selenium sulfate. The chlorhexidine salt may be selected from any of a group of C1 to C6 monocarboxylic acids and mixtures thereof.

While not limited to these, the following specific composition examples in Table 2 have been found to be especially effective in eliminating and/or preventing thrush in horses.

TABLE 2

| | Percent by Weight | |
| --- | --- | --- |
| Component | Ex. A | Ex. B |
| Chlorhexidine diacetate | 1.5 | 1.5 |
| Copper sulfate | 30.0 | 50.0 |
| Petrolatum | 68.5 | None |
| Xanthan gum | None | 1.5 |
| Isopropanol | None | 3.0 |
| Deionized water | None | 44.0 |

The A and B compositions are both effective in treating thrush, but the B formulation is preferred due to greater ease in compounding all the ingredients together into a homogeneous blend. It also is less sensitive to the extremes of the temperature range of use, and can be applied to a hoof that is still wet.

In an alternative embodiment, the composition of the viscous carrier is a solution of xanthan gum, alcohol, and water. Most preferably, the composition of the viscous carrier solution is about 2.5 percent by weight xanthan gum, about 5 percent by weight isopropanol, and about 92.5 percent by weight water. With the water-based viscous carrier, the preferred composition comprises a) a chlorhexidine salt in a range of 1.5 to 2.0 percent by weight;
b) a copper sulfate in a range of 45 to 65 percent by weight; and
c) an aqueous viscous carrier comprising a balance of said composition. More specifically, a preferred aqueous carrier includes:
a) about 2.5 percent by weight xanthan gum;
b) about 5 percent by weight isopropanol, and
c) about 92.5 percent by weight water.

While a presently preferred and various alternative embodiments of the present invention have been described in sufficient detail above to enable a person skilled in the relevant art to make and use the same, it should be obvious that various other adaptations and modifications can be envisioned by those persons skilled in such art without departing from either the spirit of the invention.

I claim:

1. A composition comprising:
   a) a chlorhexidine salt in a range of 0.1 to 5.0 percent by weight;
   b) a copper sulfate in a range of 30 to 45 percent by weight;
   c) a petrolatum based viscous carrier comprising a balance of said composition; and
   d) wherein said composition is configured to treat animal horny tissue.

2. The composition, according to claim 1, wherein said chlorhexidine salt is an acetate in a range of 1 to 3 percent by weight.

3. The composition, according to claim 1, wherein said chlorhexidine salt is a gluconate in a range of 1 to 3 percent by weight.

4. The composition, according to claim 1, wherein said copper sulfate composition is between 35 and 45 percent by weight.

5. The composition, according to claim 1, wherein said petrolatum based viscous carrier is a homogenous petrolatum blend containing white petrolatum.

6. The composition, according to claim 1, wherein said petrolatum based viscous carrier is one of a gel, a paste, and a combination thereof.

7. A composition comprising:
   a) a chlorhexidine salt in a range of 1.5 to 2.0 percent by weight;
   b) a copper sulfate in a range of 30 to 50 percent by weight; and
   c) a petrolatum constituting a balance of said composition.

* * * * *